(12) United States Patent
Gandhi

(10) Patent No.: US 8,836,958 B2
(45) Date of Patent: Sep. 16, 2014

(54) ENHANCED SCANNING OF TRANSPARENT FIBERS

(71) Applicant: Toyota Motor Engineering & Manufacturing North America, Inc, Erlanger, KY (US)

(72) Inventor: Umesh N. Gandhi, Farmington Hills, MI (US)

(73) Assignee: Toyota Motor Engineering & Manufacturing North America, Inc., Erlanger, KY (US)

(*) Notice: Subject to any disclaimer, the term of this patent is extended or adjusted under 35 U.S.C. 154(b) by 0 days.

(21) Appl. No.: 13/740,171

(22) Filed: Jan. 12, 2013

(65) Prior Publication Data

US 2014/0198309 A1 Jul. 17, 2014

(51) Int. Cl.
*G01B 11/06* (2006.01)

(52) U.S. Cl.
USPC .......................................... 356/634; 356/625

(58) Field of Classification Search
CPC ...... G01M 11/088; G01M 11/35; G02B 6/06; G02B 6/2555; G02B 6/2551; G02B 6/08; C03B 37/15
USPC .......... 356/634–635, 625, 73.1, 369, 342, 73, 356/496, 503, 432; 65/484, 158, 435, 378; 385/28, 125–126; 250/227.29–227.3
See application file for complete search history.

(56) References Cited

U.S. PATENT DOCUMENTS

| | | | |
|---|---|---|---|
| 5,017,312 A | 5/1991 | Peters et al. | |
| 5,846,356 A | 12/1998 | Vyakarnam et al. | |
| 6,025,285 A | 2/2000 | Vyakarnam et al. | |
| 7,382,500 B2 | 6/2008 | Payne | |
| 2009/0214166 A1* | 8/2009 | Huang et al. | 385/96 |

FOREIGN PATENT DOCUMENTS

WO 84/04159 10/1984

* cited by examiner

*Primary Examiner* — Tri T Ton
(74) *Attorney, Agent, or Firm* — Christopher G. Darrow; Young Basile Hanlon & MacFarlane, P.C.

(57) ABSTRACT

An apparatus and methods for scanning and measuring transparent fibers. One example method includes placing the transparent fibers on a platen of a flat-bed style scanner and compressing the transparent fibers to the platen with a cover including a non-reflective surface adjacent to the transparent fibers. The method also includes spacing an image sensor apart from a light source on a carriage below the platen and transmitting light from the light source through the platen. The light refracts within the transparent fibers and reflects from the transparent fibers to the image sensor and is absorbed by the non-reflective surface of the cover. The method also includes capturing an image of the transparent fibers with the image sensor.

16 Claims, 3 Drawing Sheets

ENHANCED SCANNING OF TRANSPARENT FIBERS

BACKGROUND

A fiber reinforced polymer (FRP) is a composite material including a polymer matrix reinforced with fibers such as glass, carbon, or plastic to improve the strength, rigidity, and impact resistance of the polymer. The properties of an FRP are dependent on the fiber length, fiber distribution, and fiber orientation within the polymer matrix. To optimize one or more properties of the FRP, the fibers present in various samples of the FRP can be measured. The fibers can be separated from the polymer matrix using heat. The fibers can then be spread on the platen of a flat-bed style scanner. The scanner can provide an image for use in measuring the lengths of the fibers present. If the fibers are transparent or near transparent, for example, when the fibers are glass or plastic, light from a light source below the platen can pass through the fiber, reflect from a cover of the scanner, and pass back through the fiber without providing sufficient contrast within the image to distinguish between the fibers for image processing.

SUMMARY

An apparatus and method for scanning and measuring transparent fibers.

One aspect of the disclosed embodiments is a method of scanning transparent fibers. The method includes placing the transparent fibers on a platen of a flat-bed style scanner; compressing the transparent fibers to the platen with a cover including a non-reflective surface adjacent to the transparent fibers; spacing an image sensor apart from a light source on a carriage below the platen; transmitting light from the light source through the platen wherein the light refracts within the transparent fibers and reflects from the transparent fibers to the image sensor and is absorbed by the non-reflective surface of the cover; and capturing an image of the transparent fibers with the image sensor.

Another aspect of the disclosed embodiments is an apparatus for scanning transparent fibers. The apparatus includes a carriage; a light source disposed on the carriage; an image sensor disposed on the carriage and spaced apart from the light source wherein the spacing between the image sensor and light source allows light to both refract within the transparent fibers and be reflected from the transparent fibers to the image sensor; a platen disposed above the carriage for receiving the transparent fibers; and a cover including a non-reflective surface disposed above the platen.

Another aspect of the disclosed embodiments is a method of measuring lengths of transparent fibers. The method includes compressing the transparent fibers to a platen of a flatbed-style scanner; transmitting light from a light source through the platen wherein the light refracts within the transparent fibers and reflects from the transparent fibers to an image sensor spaced from the light source; capturing an image of the transparent fibers with the image sensor; and processing the image to measure the lengths of the transparent fibers.

BRIEF DESCRIPTION OF THE DRAWINGS

The description herein makes reference to the accompanying drawings wherein like reference numerals refer to like parts throughout the several views, and wherein.

DETAILED DESCRIPTION

The material properties of an FRP are dependent upon fiber length, fiber distribution, and fiber orientation within the polymer matrix. The fibers within the polymer matrix can be small and lightweight; in some applications the fibers vary from one-half to six millimeters in length and ten to twenty microns in width. The fibers can also be transparent, made of glass or plastic. Measuring the length of small, transparent fibers can require optimizing an existing imaging system, such as a flat-bed style scanner, to account for both the small scale and transparency of the fibers. Accuracy of a length measurement can be improved by using a non-reflective cover to compress the fibers to a platen of a flat-bed style scanner and a spaced light source and image sensor disposed on a carriage to transmit and capture light reflected from and refracted within the fibers.

Figure 1:
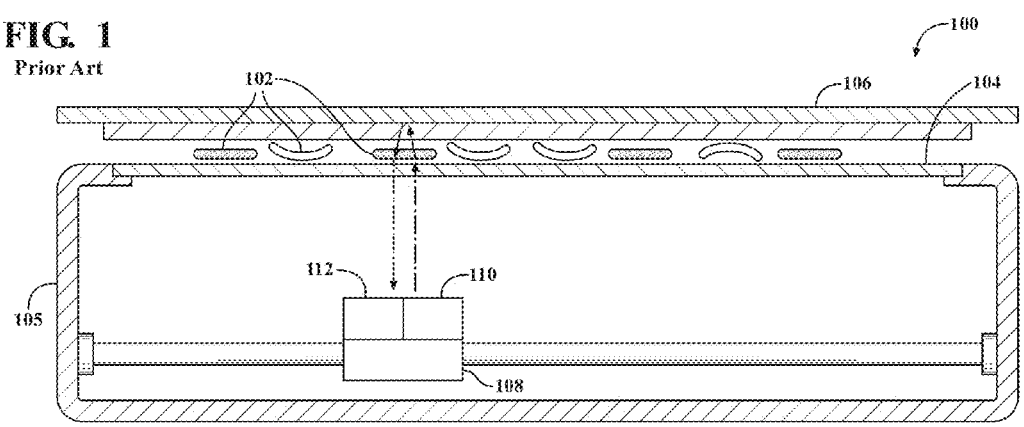
FIG. 1 is a cross-section view of a flat-bed style scanner with transparent fibers disposed on the platen in accordance with the prior art.

FIG. 1 is a cross-section view of a flat-bed style scanner 100 with transparent fibers 102 disposed on a platen 104 in accordance with the prior art. The platen 104 can be disposed on a top surface of a housing 105. The scanner 100 can also include a cover 106 disposed above the platen 104 and the transparent fibers 102. Some of the transparent fibers 102 disposed on the platen 104 are lying flat against the platen 104. Other transparent fibers 102 are curled, with the ends of the transparent fibers 102 either curling toward or curling away from the platen 104. The cover 106 on the prior-art flat-bed style scanner 100 is not positioned or weighted to sufficiently compress the transparent fibers 102 to the platen 104.

The flat-bed style scanner 100 can also include a carriage 108 disposed within the housing 105. The carriage 108 can include means of traversing the housing 105, that is, means of traveling between a first position and a second position. The means can include wheels, drive chains, drive wires, magnets, or any other method of moving the carriage 108 between the first and second positions within the housing 105.

The flat-bed style scanner 100 can also include a light source 110 and an image sensor 112 disposed adjacent to each other on the carriage 108. An image can be captured by the image sensor 112 with contrast provided by light transmitted and reflected from the light source 110. An example light transmission path is shown in dotted-line arrows to detail how light is transmitted by the light source 110 and captured by the image sensor 112 during a traditional scan using the prior-art flat-bed style scanner 100. Light can be transmitted from the light source 110, transmitted through the platen 104, transmitted through a transparent fiber 102, reflected by the cover 106, transmitted back through the transparent fiber 102, transmitted back through the platen 104, and captured by the image sensor 112.

The cover 106 is reflective and the transparent fiber 102 is transparent or near-transparent, as is the platen 104. The transparent fibers 102 can curl toward or away from the platen 104. The image captured by the image sensor 112 is unlikely to provide sufficient contrast between the background and outline of the transparent fibers 102 to allow accurate measurement of the length of the transparent fibers 102. Further, the curl present in some of the transparent fibers 102 can lead to incorrect length measurements since the image captured is only a two-dimensional representation of the transparent fibers 102 in the plane of the platen 104.

Figure 2:
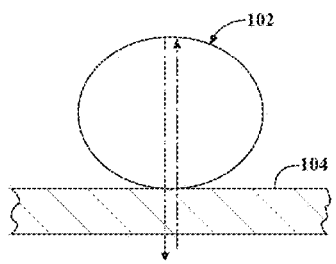
FIG. 2 is a detail view showing a light transmission path through a transparent fiber on the flat-bed style scanner of FIG. 1.

FIG. 2 is a detail view showing a light transmission path through a transparent fiber 102 disposed on the platen 104 of the flat-bed style scanner 100 of FIG. 1. When light transmitted through the platen 104 enters the transparent fiber 102 it does so at an incidence almost perpendicular to the surface of the platen 104. Light then travels straight through the transparent fiber 102 and is reflected either by the top of the transparent fiber 102 as shown, or by the reflective cover 106 (not shown). Light then travels back through the transparent fiber 102 and back through the platen 104 to be captured by the image sensor 112.

If light travels in the manner shown in FIG. 2, the transparent fiber 102 is not likely to appear distinctly in an image captured by the image sensor 112. It can be difficult to see the transparent fiber 102 in the image because the transparent fiber 102 and background of the image may have the same level of brightness. The travel of light through the transparent fiber 102 at only a single location may make the width of the transparent fiber 102 difficult to discern. The overall length of the transparent fiber 102 may not be able to be calculated, especially if the ends of the transparent fiber 102 are curled. An improved method and apparatus for scanning and measuring the length of transparent fibers that alleviates these problems is described in FIGS. 3-5.

Figure 3:
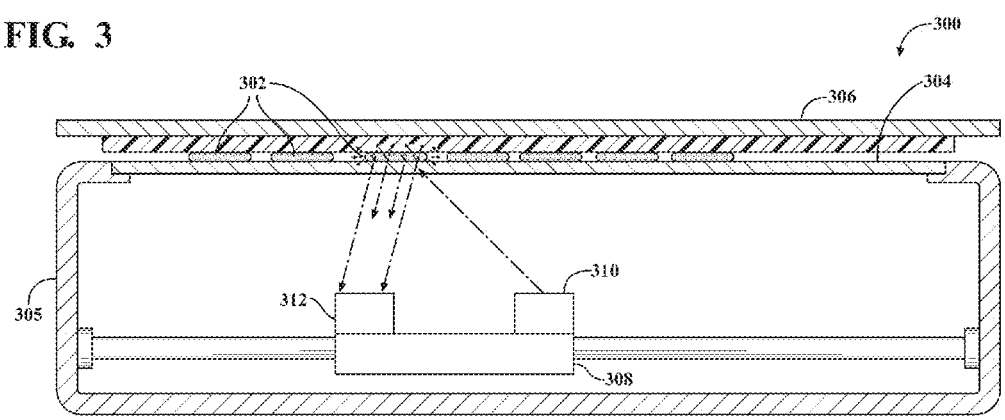
FIG. 3 is a cross-section view of a flat-bed style scanner with transparent fibers disposed on the platen in accordance with one or more embodiments described here.

FIG. 3 is a cross-section view of a flat-bed style scanner 300 with transparent fibers 302 disposed on the platen 304 in accordance with one or more embodiments described here. The platen 304 can be disposed on a top surface of a housing 305. The scanner 300 can also include a cover 306 disposed above the platen 304 and the transparent fibers 302. The cover 306 can include a non-reflective and/or light-absorbing surface adjacent to the transparent fibers 302. The cover 306 can be constructed of light-absorbing glass to absorb light passing through the transparent fibers 302. Light-absorbing glass, for example, can be used to minimize adhesion between the transparent fibers 302 and the cover 306.

The cover 306 can also have sufficient mass to flatten the transparent fibers 302 to the platen 304 when disposed above the platen 304. Alternatively, the cover 306 can include latching means (not shown) to force compression of the transparent fibers 302 to the platen 304. By compressing the transparent fibers 302 to the platen 304, the full length of each transparent fiber 302 is coincident with the platen 304.

The flat-bed style scanner 300 can also include a carriage 308 disposed within the housing 305. The carriage 308 can include means of traversing the housing 305, that is, means of traveling between a first position and a second position. The means can include wheels, drive chains, drive wires, magnets, or any other method of moving the carriage 308 between the first and second positions within the housing 305.

The flat-bed style scanner 300 can also include a light source 310 and an image sensor 312 disposed on the carriage 308. The light source 310 and image sensor 312 can be spaced apart a sufficient distance to allow light to both refract within the transparent fibers 302 and be reflected from the transparent fibers 302 to the image sensor 312.

An image can be captured by the image sensor 312 with contrast provided by light transmitted and reflected from the light source 310. Example light transmission paths are shown in dotted-line arrows to detail how light is transmitted by the light source 310 and captured by the image sensor 312 using the improved flat-bed style scanner 300. Light can be transmit from the light source 310, transmit through the platen 104, refract within and reflect from the walls of the transparent fiber 302, transmit back through the platen 304, and be captured by the image sensor 312. Because the cover 306 is non-reflective, any light reflected from the transparent fiber 302 toward the cover 306 is absorbed by the cover 306.

Figure 4:
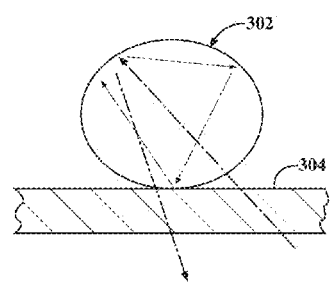
FIG. 4 is a detail view showing a light transmission path through a transparent fiber on the flat-bed style scanner of FIG. 3.

FIG. 4 is a detail view showing example light transmission paths through a transparent fiber 302 on the improved flat-bed style scanner 300 of FIG. 3. When light transmitted through the platen 304 enters the transparent fiber 302, it does so at an angle sufficient to direct the light toward an outer portion of the diameter of the transparent fiber 302. Light can then reflect from the wall of the transparent fiber 302 in several directions. Light is reflected for transmission back through the platen 304 toward the image sensor 312. Light is also refracted within the transparent fiber 302. Refracted light can exit the ends of the transparent fiber 302 to be absorbed by the cover 306 or transmitted through the platen 304 to be captured by the image sensor 312.

If light travels in the manner shown in FIG. 4, the transparent fiber 302 can be easily distinguished in an image captured by the image sensor 312. The background of the image can vary greatly in contrast to the outer edges of the transparent fiber 302, indicating width of the transparent fiber 302. The background of the image can also vary greatly in contract to the ends of the transparent fiber 302; the ends can appear as bright, distinct features within the image because of the refraction of light within the transparent fiber 302. The overall length of the transparent fiber 302 will be straightforward to calculate using image processing software. Further, the length will be accurate because the ends of the transparent fiber 102 are flattened to the platen 304 by the cover 306.

Figure 5:
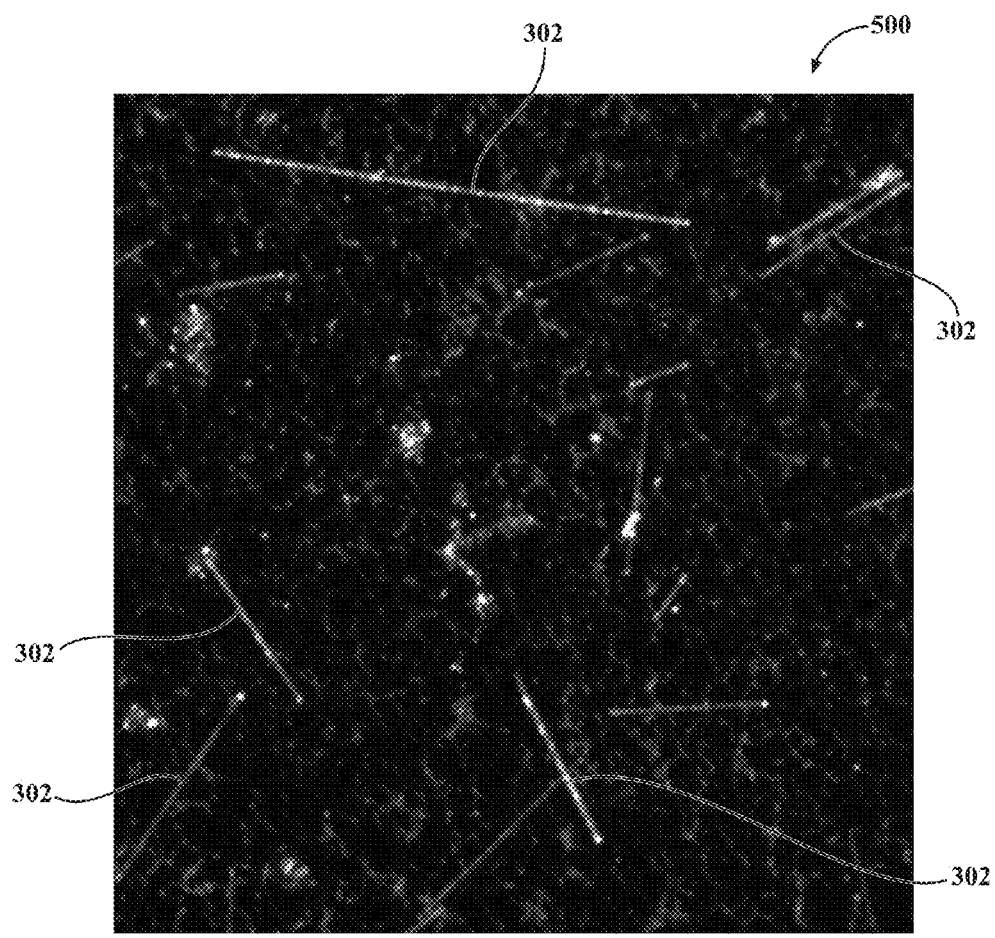
FIG. 5 is an example image of the transparent fibers produced by the flat-bed style scanner shown in FIG. 3.

FIG. 5 is an example image 500 of the transparent fibers 302 produced by the improved flat-bed style scanner 300 shown in FIG. 3. The background of the image 500 appears very dark. This appearance is due to the light-absorbing features of the cover 306 shown in FIG. 3. Multiple transparent fibers 302 appear in a variety of lengths throughout the image 500. The beginning and ending of each transparent fiber 302 can be discerned by the bright ends. The ends of the transparent fibers 302 appear bright in the image 500 because light exits the transparent fibers 302 at the ends after refracting within the transparent fibers 302.

Each transparent fiber 302 in the image 500 is straight or nearly straight. The cover 306 compresses the transparent fibers 302 to the platen 304, removing any tendency of the small transparent fibers 302 to curl toward or away from the platen 304. Once the image 500 is captured, it can be processed using software capable of counting and measuring the length of the transparent fibers 302 present in the image. This information can be used to determine the physical properties of the FRP being inspected.

One example method of implementing the improved flat-bed style scanner 300 described in FIGS. 3-5 above includes placing the transparent fibers 302 on a platen 304 of a flat-bed style scanner 300 and compressing the transparent fibers 302 to the platen 304 with a cover 306 including a non-reflective surface adjacent to the transparent fibers 302. As described above, the cover 306 can comprise light-absorbing glass having sufficient mass to flatten the transparent fibers 302 to the platen 304 when disposed above the platen 304.

The method can also include spacing an image sensor 312 apart from a light source 310 on a carriage 308 disposed below the platen 304. As described above, the spacing between the image sensor 312 and light source 310 allows light to both refract within the transparent fibers 302 and be reflected from the transparent fibers 302 to the image sensor 312. The method can also include transmitting light from the light source 310 through the platen 304 wherein the light refracts within the transparent fibers 302 and reflects from the transparent fibers 302 to the image sensor 312 and is absorbed by the non-reflective surface of the cover 306.

The method can also include capturing an image, such as image 500 shown in FIG. 5, of the transparent fibers 302 with the image sensor 312. The transparent fibers 302 include ends and the image 500 of the transparent fibers 302 shows the ends having high levels of contrast as compared to a background of the image 500 based on the refraction of light within the transparent fibers 302. In the image 500 in FIG. 5, the high level of contrast is between the dark background and the bright, light ends of the transparent fibers 302. The image sensor 312 can capture the image 500 of the transparent fibers 302 while the carriage travels between a first position and a second position within the housing 305 of the scanner 300.

The method can also include processing the image to measure the lengths of the transparent fibers 302. Image processing can be accomplished using a variety of software. For example, the length of each transparent fiber 302 can be calculated by measuring between each bright end of each transparent fiber 302 since the ends have a high level of contrast as compared to the background of the image 500. As seen in FIG. 5, it is possible to distinguish each transparent fiber 302 from the background and from other transparent fibers 302 using the bright ends and highlighted bodies of the transparent fibers 302 between the ends.

Another example method of implementing the improved flat-bed style scanner 300 described in FIGS. 3-5 can include compressing the transparent fibers 302 to the platen 304 of a flatbed-style scanner 300 and transmitting light from a light source 310 through the platen 304 so that the light refracts within the transparent fibers 302 and reflects from the transparent fibers 302 to an image sensor 312 spaced from the light source 310. The spacing between the image sensor 312 and light source 310 is sufficient to allow light to both refract within the transparent fibers 302 and be reflected from the transparent fibers 302 to the image sensor 312.

The method can also include capturing an image, such as image 500 in FIG. 5, of the transparent fibers 302 with the image sensor 312. The image 500 of the transparent fibers can show that ends of the transparent fibers 302 have high levels of contrast to a background of the image 500 because of the refraction of light within the transparent fibers 302. The method can also include processing the image 500 to measure the lengths of the transparent fibers 302. The measurement can be based on the ends having the high levels of contrast as compared to the background of the image 500.

Each of the above methods can be implemented on a flat-bed style scanner 300 apparatus as shown in FIG. 3. The scanner 300 can include a carriage 308 and a light source 310 disposed on the carriage. The scanner 300 can also include an image sensor 312 disposed on the carriage 308 and spaced apart from the light source wherein the spacing between the image sensor 312 and light source 310 allows light to both refract within the transparent fibers 302 and be reflected from the transparent fibers 302 to the image sensor 312. The carriage 308 can include means for traveling between a first position and a second position as described above.

The scanner 300 can also include a platen 304 disposed above the carriage 308 for receiving the transparent fibers 302 and a cover 306 including a non-reflective surface disposed above the platen 304. As described above, the cover 306 can include means for compressing the transparent fibers 302 to the platen 304. The means can be light-absorbing glass having sufficient mass to flatten the transparent fibers 302 to the platen 304 when disposed above the platen 304. The non-reflective surface of the cover 306 can be located adjacent to the platen 304 when in a closed position to absorb any light passing through or reflecting toward the cover 306 from the transparent fibers 302.

The foregoing description relates to what are presently considered to be the most practical embodiments. It is to be understood, however, that the disclosure is not to be limited to these embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method of scanning transparent fibers, comprising:
    placing the transparent fibers on a platen of a flat-bed style scanner;
    compressing the transparent fibers to the platen with a cover including a non-reflective surface adjacent to the transparent fibers;
    spacing an image sensor apart from a light source on a carriage below the platen;
    transmitting light from the light source through the platen wherein the light refracts within the transparent fibers and reflects from the transparent fibers to the image sensor and is absorbed by the non-reflective surface of the cover; and
    capturing an image of the transparent fibers with the image sensor.

2. The method of claim 1 wherein the cover comprises light-absorbing glass having sufficient mass to flatten the transparent fibers to the platen when disposed above the platen.

3. The method of claim 1 wherein the spacing between the image sensor and light source allows light to both refract within the transparent fibers and be reflected from the transparent fibers to the image sensor.

4. The method of claim 1 wherein the transparent fibers include ends and the image of the transparent fibers shows the ends having high levels of contrast as compared to a background of the image based on the refraction of light within the transparent fibers.

5. The method of claim 4, further comprising:
    processing the image to measure lengths of the transparent fibers using the ends having the high levels of contrast as compared to the background of the image.

6. The method of claim 1 wherein the carriage includes means for traveling between a first position and a second position.

7. The method of claim 6 wherein the image sensor captures the image of the transparent fibers while the carriage travels between the first position and the second position.

8. An apparatus for scanning transparent fibers, comprising:
    a carriage;
    a light source disposed on the carriage;
    an image sensor disposed on the carriage and spaced apart from the light source;

a platen disposed above the carriage for receiving the transparent fibers; and a cover including a non-reflective surface disposed above the platen, the cover having sufficient mass to compress the transparent fibers to the platen;

wherein the light source transmits light through the platen and wherein the light refracts within the transparent fibers and reflects from the transparent fibers and is absorbed by the non-reflective surface of the cover.

9. The apparatus of claim 8 wherein the cover comprises light-absorbing glass having sufficient mass to flatten the transparent fibers to the platen when disposed above the platen.

10. The apparatus of claim 8 wherein the non-reflective surface of the cover is located adjacent to the platen.

11. The apparatus of claim 8 wherein the carriage including means for traveling between a first position and a second position.

12. The apparatus of claim 11 wherein the image sensor captures an image of the transparent fibers while the carriage travels between the first position and the second position.

13. The apparatus of claim 12 wherein the transparent fibers include ends and the image of the transparent fibers shows the ends having high levels of contrast to a background of the image based on the refraction of light within the transparent fibers.

14. The apparatus of claim 13 wherein the image can be processed to measure lengths of the transparent fibers using the ends having the high levels of contrast as compared to the background of the image.

15. A method of measuring lengths of transparent fibers, comprising:

compressing the transparent fibers to a platen of a flatbed-style scanner to flatten the transparent fibers to the platen;

transmitting light from a light source through the platen wherein the light refracts within the transparent fibers and reflects from the transparent fibers to an image sensor spaced from the light source;

capturing an image of the transparent fibers with the image sensor; and processing the image to measure the lengths of the transparent fibers; and wherein the lengths of the transparent fibers are measured based on ends of the transparent fibers having high levels of contrast to a background of the image based on the refraction of light within the transparent fibers.

16. The method of claim 15 wherein the spacing between the image sensor and light source allows light to both refract within the transparent fibers and be reflected from the transparent fibers to the image sensor.

\* \* \* \* \*